United States Patent
Pitkin

(10) Patent No.: US 8,992,615 B2
(45) Date of Patent: Mar. 31, 2015

(54) IN-BONE IMPLANTABLE SHAFT FOR PROSTHETIC JOINTS OR FOR DIRECT SKELETAL ATTACHMENT OF EXTERNAL LIMB PROSTHESES AND METHOD OF ITS INSTALLATION

(71) Applicant: Mark Pitkin, Sharon, MA (US)

(72) Inventor: Mark Pitkin, Sharon, MA (US)

( * ) Notice: Subject to any disclaimer, the term of this patent is extended or adjusted under 35 U.S.C. 154(b) by 0 days.

(21) Appl. No.: 14/050,523

(22) Filed: Oct. 10, 2013

(65) Prior Publication Data

US 2014/0135942 A1   May 15, 2014

Related U.S. Application Data

(63) Continuation of application No. 11/899,068, filed on Sep. 5, 2007, now abandoned.

(51) Int. Cl.
*A61F 2/28*    (2006.01)
*A61F 2/30*    (2006.01)
*A61B 17/15*   (2006.01)
(Continued)

(52) U.S. Cl.
CPC .................. *A61F 2/30* (2013.01); *A61F 2/4644* (2013.01); *A61L 2430/02* (2013.01); *A61F 2/28* (2013.01); *A61B 17/15* (2013.01); *A61B 17/7258* (2013.01); *A61F 2/30721* (2013.01); *A61F 2/30749* (2013.01); *A61F 2/78* (2013.01); *A61F 2002/30434* (2013.01); *A61F 2002/30848* (2013.01); *A61F 2002/30884* (2013.01); *A61F 2002/30892* (2013.01); *A61F 2002/30899* (2013.01); *A61F 2002/7887* (2013.01); *A61F 2220/0041* (2013.01)
USPC ...................................... 623/16.11; 623/23.5

(58) Field of Classification Search
CPC ......................................................... A61F 2/28
USPC .............................................. 623/16.11, 23.5
See application file for complete search history.

(56) References Cited

U.S. PATENT DOCUMENTS 2,765,787 A    10/1956    Pellet
3,996,625 A    12/1976    Noiles
(Continued)

OTHER PUBLICATIONS

Jae-Young Rho et al.; Mechanical properties and the hierarchical structure of bone; Medical Engineering & Physics (1998) 20, 92-102.
(Continued)

*Primary Examiner* — Jacqueline Woznicki
(74) *Attorney, Agent, or Firm* — McLane, Graf, Raulerson & Middleton, PA

(57) ABSTRACT

An in-bone implantable shaft for prosthetic joints or for direct skeletal attachment of external limb prostheses, comprised of a central body fitted in the zone of the bone's medullary cavity conventionally prepared for implantation, and of side elements attached to the central body and fitted in the slots specially made in the bone's walls surrounding said medullary canal; said side elements have spaces between them, arranged to be filled by bone cells to provide a natural and safe osseolocking of the shaft. A method of preparing the bone for implantation of a prosthetic shaft, comprising the steps of: placing a cylindrical guide with slots made in the longitudinal direction of said guide inside said bone's canal which is conventionally prepared for implantation; cutting said bone's walls by progressing a saw along the edges of the slots of said guide; removing the guide; fitting the shaft in the bone's canal, provided that the side elements are fitted to the slots in the bone's walls.

16 Claims, 3 Drawing Sheets

(51) Int. Cl.
*A61F 2/78* (2006.01)
*A61F 2/46* (2006.01)
*A61B 17/72* (2006.01)

(56) References Cited

U.S. PATENT DOCUMENTS

| | | | |
|---|---|---|---|
| 4,164,794 A | 8/1979 | Spector et al. | |
| 4,231,120 A | 11/1980 | Day | |
| 4,403,607 A | 9/1983 | Woo et al. | |
| 4,608,053 A * | 8/1986 | Keller | 623/23.31 |
| 4,828,566 A | 5/1989 | Griss | |
| 4,938,770 A | 7/1990 | Frev et al. | |
| 5,324,199 A | 6/1994 | Branemark | |
| 5,480,453 A * | 1/1996 | Burke | 623/23.21 |
| 5,658,351 A | 8/1997 | Dudasik et al. | |
| 5,702,445 A | 12/1997 | Branemark | |
| 5,716,361 A * | 2/1998 | Masini | 606/86 R |
| 6,159,216 A | 12/2000 | Burkinshaw et al. | |
| 6,290,724 B1 | 9/2001 | Marino | |
| 6,290,726 B1 * | 9/2001 | Pope et al. | 623/22.15 |
| 6,436,139 B1 | 8/2002 | Shapiro et al. | |
| 6,520,966 B1 | 2/2003 | Kohler et al. | |
| 6,558,423 B1 | 5/2003 | Michelson | |
| 6,740,120 B1 | 5/2004 | Grimes | |
| 6,752,833 B2 | 6/2004 | Hesseling et al. | |
| 7,001,394 B2 | 2/2006 | Gundlapalli et al. | |
| 7,041,135 B2 | 5/2006 | Michelson | |
| 7,056,342 B2 | 6/2006 | Michelson | |
| 7,556,648 B2 | 7/2009 | Picha et al. | |
| 2001/0047207 A1 | 11/2001 | Michelson | |
| 2002/0099381 A1 | 7/2002 | Maroney | |
| 2002/0099445 A1 | 7/2002 | Maroney et al. | |
| 2002/0193881 A1 | 12/2002 | Shapiro et al. | |
| 2003/0078668 A1 | 4/2003 | Michelson | |
| 2003/0199983 A1 | 10/2003 | Michelson | |
| 2004/0176854 A1 | 9/2004 | Hesseling et al. | |
| 2005/0143827 A1 | 6/2005 | Globerman et al. | |
| 2005/0177241 A1 | 8/2005 | Angibaud et al. | |
| 2007/0050032 A1 | 3/2007 | Gittings et al. | |
| 2007/0050033 A1 | 3/2007 | Reo et al. | |
| 2007/0198088 A1 | 8/2007 | Biedermann et al. | |
| 2007/0255421 A1 | 11/2007 | Dickson | |
| 2007/0282443 A1 | 12/2007 | Globerman et al. | |
| 2008/0033569 A1 | 2/2008 | Ferren et al. | |

OTHER PUBLICATIONS

Peter Munger et al.; Patient-related risk factors leading to aseptic stem loosening in total hip arthroplasty; ActaOrthopaedica (2006) 77(4),567-574.

* cited by examiner

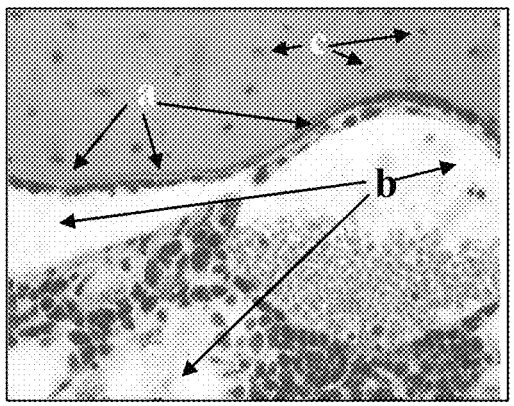

Figure 1. (a) Endosteum, the internal lining of the medullary cavity (b) composed of reticular tissue osteogenic cells; (c) osteocytes of the compact bone tissues surrounding medullary cavity.

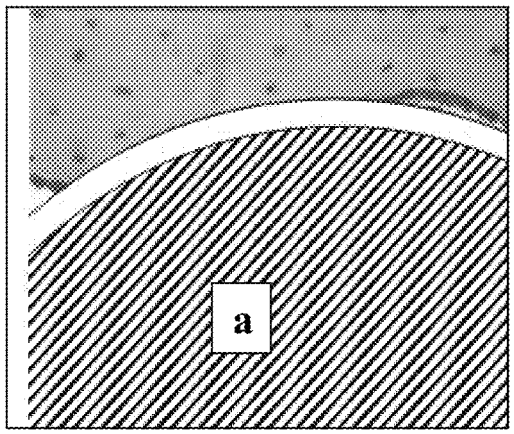

Figure 2. Preparation of the medullar cavity (see Fig. 1) with the drill (a) for inserting the implant's stem.

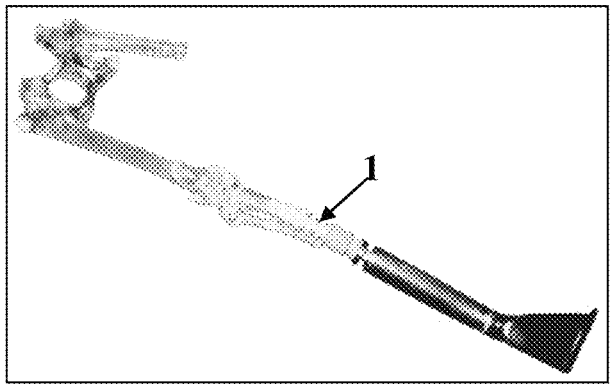

Figure 3. Screws (1) to secure the implanted shaft of the prosthesis:
http://www.engr.ncsu.edu/news/newsletters/pdfs/frontline_1105.pdf.

IN-BONE IMPLANTABLE SHAFT FOR PROSTHETIC JOINTS OR FOR DIRECT SKELETAL ATTACHMENT OF EXTERNAL LIMB PROSTHESES AND METHOD OF ITS INSTALLATION

CROSS REFERENCE TO RELATED APPLICATIONS

This application claims the benefit under 35 U.S.C. §120 of U.S. application Ser. No. 11/899,068, filed Sep. 5, 2007, the entire disclosure of which is incorporated herein by reference.

TECHNICAL FIELD

Prosthetics, surgical instruments; more particularly, methods and devices for surgically preparing a bone for the implantation of a prosthetic implant component of a prosthetic joint [1, 2] or the implantation of an abutment for direct skeletal attachment of external prostheses, as described in: http://www.sahlgrenska.se/vgrtemplates/Page 33031.aspx.

BACKGROUND OF THE INVENTION

This invention relates to prosthetic implants for skeletal replacement, reconstruction and attachment in humans and animals, and, more particularly, to the design and method of installation of such devices that would reduce their loosening with time.

Implantable devices are used to partially or completely replace joints or bone segments in humans and animals, or to provide direct skeletal attachment of external prostheses to the residuum.

The known approaches to attaching the implants include fitting the implant into the medullary canal of the bone by force; securing the implant in the bone with screws or pins; bonding the implant to the bone with various adhesives; use of porous structures to stimulate ingrowth of the bone into the implant's surface.

One of the major problems involved in the use of such devices is the loosening of the attachment between the prosthetic implant and the associated bone. Loosening occurs mainly due to the cyclical application of bending moments during locomotion which eventually destroy the bond between the implant and the bone [3-5].

To decrease loosening, a more precise installation technique, anchoring elements, and surgical assemblies were introduced in U.S. Pat. Nos. 5,702,445 [6], 6,159,216 [7], 6,520,966 [8], and 7,001,394 [9]. Another approach was introduced in U.S. Pat. No. 4,828,566 where a recess is carved from the implanted region of the prosthesis in the proximal medial region, and a U-shaped wire mesh structure is fitted within the recess. The wire mesh structure allows for an ingrowth of bone tissue in the medial narrow side of the shank and for the absorption of shear micro movements between the bone and the implant [10].

One of the reasons for loosening, after all these approaches or their several combinations are used, is that the approaches are all in conflict with the structure and function of the medullary cavity canal, into which the implants are inserted. With the conventional method of installation of the shank, a drill first bores the tube bone to prepare an area into which the shaft of the implant fits exactly. Then, the implant is installed into the bone as described in: http://biomedtrix.com/sur.html.

The procedure destroys, completely or in part, the layer of endosteal bone trabeculae, or endosteum, which fills the medullary cavity of the bone [11], as illustrated in FIGS. 1 and 2.

After the medullary canal is drilled (see FIG. 2) in preparation for device implantation, osteocytes begin to remodel the internal canal walls and fill the gaps between the implant and the walls, including the specially designed cavities or pores in the implant. The remodeling proceeds in the direction out from the outer walls toward the interior walls of the medullary canal [12].

Such ossification fixes the implant inside the bone canal by developing multiple micro locks, and is therefore useful for anchoring and preventing further loosening. However, the pre-existing position of the endosteum limits the potential volume of the remodeled ossified bone tissue in the outward-inward direction. This is the natural mechanism which protects the area designated for bone marrow from filling with cortical bone, in the process of bone remodeling as a consequence of bone fracture [12].

Therefore for additional anchoring, to augment the effects of slight ossification, the implant is often secured with screws (1) (see FIG. 3) inserted from the outside of the bone into the implanted shaft of the prosthesis, as described in:
http://www.engr.ncsu.edu/news/newsletters/pdfs/frontline 1105.pdf.

This locking and anchoring approach requires additional operation time and techniques for exact positioning of the screws relative to the holes of the shaft implanted into the medullary canal.

All described approaches depend on ossification inside the medullary canal, which has aforementioned natural limitations to the volume of the remodeled bone tissues.

In contrast to ossification in the outer-to-inner direction, the ossification in the direction of the longitudinal axis of a bone can be achieved in significantly higher volumes of remodeled bone tissues. This well-known phenomenon is utilized in bone lengthening techniques, when an external apparatus is applied for the fixation of the bone fragments that are created after the bone is dissected perpendicularly to its longitudinal axis. Then, with the aid of the given external apparatus, bone fragments are moved apart 1-2 mm per day. Continued ossification, when properly controlled, allows the bone to lengthen up to 33% of its original length [13, 14]. Similar volume of ossification occurs in the lateral direction when the bone is widened [15]. However, this approach has never been applied to lock the implanted shaft.

Accordingly, it is an object of the present invention to prevent the occurrence of the implant loosening. It is another object of the invention to utilize the natural anchoring (osseolocking) of an implant in a bone by introducing a corresponding device and method of its installation.

BRIEF SUMMARY OF THE INVENTION

The present invention relates to the creation of favorable conditions for the ingrowth of bone cells and tissues between and throughout the sides of the implanted shaft ("osseolocking"). To increase the positive effect of osseolocking, the bone walls are specially prepared in conjunction with the standard drilling of the medullary canal. That specific preparation includes fashioning one or more slots in the bone walls in the longitudinal direction. The protruding sides of the installed implant are positioned in the slots, and the ossification begins. That ossification process between and throughout the side elements progresses in the direction of the widening bone, and is able to naturally lock the implant's shaft with an anchoring effect similar to the inter-locking nailing, but without its complications [16].

Another object of the present invention is the method of preparing a bone for the implantation of a prosthetic shaft, which consists of the following steps: placing a cylindrical guide with slots in the longitudinal direction into the bone's canal already conventionally prepared for implantation; cutting the bone's walls by progressing a saw along the sides of the slots in the guide; removing the guide; fitting the shaft into the bone's canal, provided that the protruding side elements are fitted into the slots in the bone's walls.

BRIEF DESCRIPTION OF THE DRAWINGS

The invention is explained in greater detail in the following description of one of the preferred embodiments of the invention with references to the accompanying figures:

FIG. 1 presents (a) endosteum, the internal lining of the medullary cavity (b) composed of reticular tissue osteogenic cells; (c) osteocytes of the compact bone tissues surrounding medullary cavity.

FIG. 2 presents preparation of the medullar cavity (see FIG. 1) with a drill (a) for inserting an implant's shaft.

FIG. 3 presents screws (1) to secure the implanted shaft of the prosthesis.

DETAILED DESCRIPTION OF THE INVENTION

Figure 4:
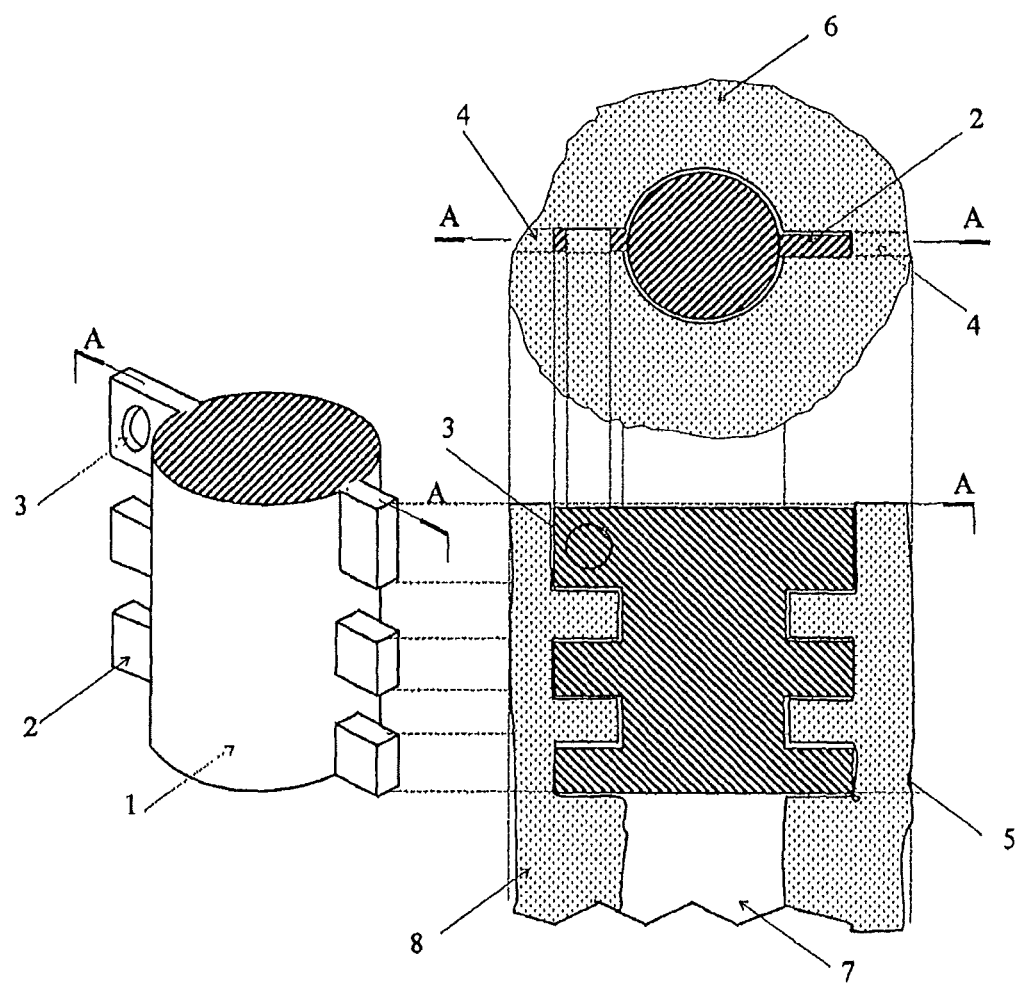
FIG. 4 present a 3D view of the shaft with central part 1 and protruding side elements 2. The elements 2 are separated from each other by open spaces, and can each be of different shape, with or without one or more holes 3, and either solid, porous, composite or meshed in composition. The partially sectioned side view of the bone 6 with the implanted shaft 1 shows newly ossified zones 3 and 5 of the bone's walls 8, and serves to demonstrate how the device is integrated with the bone at the end of the healing process. The top view shows the shaft 1 after healing, following the shaft's installation into the pre-drilled cylindrical cavity in the medullary canal, and into the pre-cut slots 4 that extend entirely through the thickness of the walls 8.

The device in the present invention, namely, the implantable shaft of the prosthetic joint or the abutment for attachment of an external limb prosthesis, has a central portion 1 situated in the cavity of the medullary canal 7 of the bone 6. The side elements 2 of this device are situated in the slots 4 pre-cut out of the walls 8 of the bone.

Figure 5:
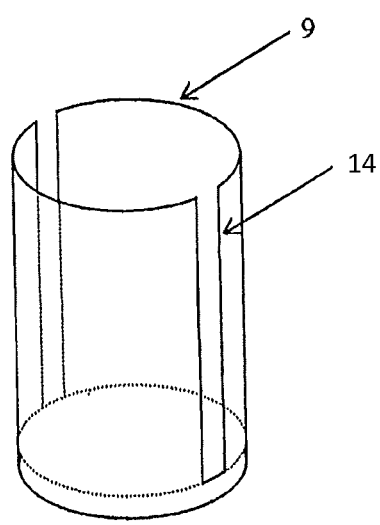
FIG. 5 presents a 3D view of a guide 9 with slots 4, which frame the interior of the section of bone to be excised from the bone walls 8, once the guide is inserted into the pre-drilled cylindrical cavity in the medullary canal (see FIG. 4).

The method of installation of the device is also a component of the present invention, and is implemented once the marrow cavity of the bone is which implantation is planned is prepared in the conventional manner (by drilling a cavity in the medullary canal 7). Specifically, a guide 9 with slots 14 (see FIG. 5) is inserted into a pre-drilled cavity in the medullary canal 7. The diameter of the drill that prepares the cylindrical cavity has to correspond to the diameter of the cavity and the depth of drilling should correspond to the height of the shaft 1 to allow the guide to be easily inserted and removed manually without additional tools. The slots 14 of the guide 9 should be oriented in the sagittal plane or otherwise depending on the patient's conditions. Then, the surgical saw is positioned against the slots of the guide and the cut is performed through the bone's walls 8 down to the limit provided by the depth of the slots 14 of the guide. Next, the guide is removed from the cavity, and the shaft 1 is implanted from the open end of the bone by positioning the side elements 2 against the slots just made in the walls 8. Insertion of the shaft should be performed carefully in order not to split the bone.

The thickness of the side elements can approximate the width of the slots and may slightly exceed the width of the slots. The width of each side element can approximate the thickness of the bone's wall such that after installation, the side elements do not extend beyond the outer circumference of the bone.

The described method of installation of the shaft activate the ossification of the bone inside the free spaces of the slots 4, which form the newly formed zones 3 and 5 with the locking effect with respect to the shaft 1 and the implant, for which the shaft 1 is a supporting element.

In other aspects, the invention relates to an implantable shaft for prosthetic joints or for direct skeletal attachment of external limb prostheses, comprised of a central body fitted in the bone's medullary cavity conventionally prepared for implantation, and of side elements attached to the central body and fitted in the slots specially made in the bone's walls surrounding the medullary canal, and the side elements have spaces between them. The side elements are lined along the longitudinal direction of the bone. The thickness of the elements approximates the width of the slots and may slightly exceed the thickness of the width of the slots. The width of each element approximates the thickness of the bone's wall such that after installation, the elements do not extend beyond the outer circumference of the bone. The invention relates to a method of preparing the bone for implantation of the prosthetic shaft, consisting of: placing a cylindrical guide with slots made in the longitudinal direction of the guide inside the bone's canal which is conventionally prepared for implantation; cutting the bone's walls by progressing a saw along the edges of the slots of the guide; removing the guide; fitting the shaft in the bone's canal, provided that the side elements are fitted to the slots in the bone's walls.

REFERENCES

1. Kang, P., Shen, B., Yang, J., Cheng, J., Pei, F., Repairing Defect and Preventing Collapse of Canine Femoral Head Using Titanium Implant Enhanced by Autogenous Bone Graft and rhBMP-2. Connect Tissue Res, 2007. 48(4): p. 171-9.
2. Shuler, M. S., Rooks, M. D., Roberson, J. R., Porous tantalum implant in early osteonecrosis of the hip: preliminary report on operative, survival, and outcomes results. J Arthroplasty, 2007. 22(1): p. 26-31.
3. Nakamura, S., Kusuzaki, K, Murata, H., Takeshita, H., Hirata, M., Hashigushi, S., Hirasawa, Y., Bone reaction induced by femoral stem of titanium alloy endoprosthesis for malignant bone tumors at the distal femur. Oncol Rep, 2001. 8(4): p. 877-81.
4. Healy, W. L., Wasilewski, S. A., Takei, R., Oberlander, M., Patellofemoral complications following total knee arthroplasty. Correlation with implant design and patient risk factors. J Arthroplasty, 1995. 10(2): p. 197-201.
5. Bini, S. A., Johnston, J. O., Martin, D. L., Compliant prestress fixation in tumor prostheses: interface retrieval data. Orthopedics, 2000. 23(7): p. 707-11; discussion 711-2.
6. Brangnemark, P.-l., Anchoring element for implantation in tissue, for holding prosthesis, artificial joint components or the like. 1997: U.S. Pat. No. 5,702,445.
7. Burkinshaw, B., Kana, R., Combination tibial preparation instrumentation 2000: U.S. Pat. No. 6,159,216.
8. Kohler, M., Trachsler, T., Schwager, W., Bohler, N., Setting instrument for a tibia part of a knee joint prosthesis 2003: U.S. Pat. No. 6,520,966.
9. Gundlapalli, R., Goldstein, W., Marcoccio, D., Mccue, D., Method and apparatus for surgically preparing a tibia for implantation of a prosthetic implant component which has an offset stem, in U.S. Pat. No. 7,001,394 2006: U.S. Pat. No. 7,001,394.
10. Griss, P., Hipjointimplant. 1989: U.S. Pat. No. 4,828,566.
11. Ham, A. W., Cormack, D. H., Ham's histology. 9th ed. 1987, Philadelphia: Lippincott. xiv, p. 732.
12. Salter, R. B., Textbook of disorders and injuries of the musculoskeletal system: an introduction to orthopaedics, fractures, and joint injuries, rheumatology, metabolic bone disease, and rehabilitation. 3rd ed. 1999, Baltimore: Williams & Wilkins. xxxiv, p. 687.
13. Yun, A. G., Severino, R., Reinker, K., Attempted limb lengthenings beyond twenty percent of the initial bone length: results and complications. J Pediatr Orthop, 2000. 20(2): p. 151-9.
14. Price, C. T., Mann, J. W., Experience with the Orthofix device for limb lengthening. Orthop Clin NorthAm, 1991. 22(4): p. 651-61.
15. Ilizarov, G. A., The tension-stress effect on the genesis and growth of tissues. Part I. The influence of stability of fixation and soft-tissue preservation. Clin Orthop, 1989 (238): p. 249-81.
16. Malik, Z. U., Hanif, M. S., Safdar, A., Masood, T., Planned external fixation to locked intramedullary nailing conversion for open fractures of shaft of femur and tibia. J Coli Physicians Surg Pak, 2005, 15(3): p. 133-6.

What is claimed is:

1. A method of preparing a bone for direct skeletal attachment of a prosthetic joint or external limb prosthesis, comprising:
    forming a cavity in the medullary canal of the bone;
    cutting one or more slots through the wall of the bone extending radially from the cavity through an entire thickness of the bone wall;
    providing an implantable shaft as part of the prosthetic joint or external limb, the shaft comprising a central body configured to fit within the cavity in the medullary canal, and a plurality of side elements extending radially outwardly from the central body, the side elements configured to fit with a portion of one or more of the slots cut through the bone wall; and
    fitting the implantable shaft in the bone, with the central body fitted within the cavity in the medullary canal, and with the plurality of side element fitted within a corresponding one or more of the slots cut entirely through the wall of the bone, with at least one open space remaining between the side element through which ossification occurs in the bone wall.

2. The method of claim 1, further comprising:
    providing a cylindrical guide having a hollow cylindrical shape and one or more slots extending in a direction of a longitudinal axis of the cylindrical guide;
    placing the cylindrical guide inside the cavity within the medullary canal; and
    cutting the one or more slots through the wall of the bone by progressing a saw along edges of the one or more slots of the cylindrical guide.

3. The method of claim 1, wherein the step of cutting one or more slots through the wall of the bone comprises cutting at least two slots through the bone wall extending longitudinally in the direction of the bone and radially outwardly from the medullary canal through the bone wall.

4. The method of claim 1, wherein the side elements have a thickness that approximates a width of the slots.

5. The method of claim 1, wherein the side elements have a thickness that slightly exceeds a width of the slots.

6. The method of claim 1, wherein the side elements have a width in a radial direction that approximates the thickness of the bone's wall.

7. A method of preparing a bone for direct skeletal attachment of a prosthetic joint or external limb prosthesis, comprising:
    providing an implantable shaft as part of the prosthetic joint or external limb, comprising:
        a central body extending longitudinally and linearly along and parallel to a straight longitudinal axis, the central body comprising a circumferential outer wall that extends linearly along and parallel to the straight longitudinal axis of the central body; and
        a plurality of side elements extending radially outwardly from the outer wall of the central body, at least two side elements of the plurality of side elements disposed in a straight linear alignment along a line that is parallel to the straight longitudinal axis of the central body, the at least two side elements spaced apart along the line to provide an open space adjacent the outer wall of the central body, the open space disposed between and in straight linear alignment with the at least two side elements;
    forming a cavity in a medullary canal of the bone configured to receive the central body of the implantable shaft;
    cutting one or more slots into a wall of the bone extending radially from the medullary canal and longitudinally parallel to the medullary canal, the one or more slots each having a longitudinal depth and radial width configured to receive a corresponding one or more of the plurality of side elements, at least one slot having a longitudinal depth sufficient to receive the at least two side elements with the one open space therebetween; and
    fitting the implantable shaft in the bone, with the central body fitted within the cavity in the medullary canal, and with the plurality of side elements fitted within a corresponding one or more of the slots cut in the wall of the bone, with the one open space remaining between the side elements through which ossification occurs in the bone wall.

8. The method of claim 7, further comprising:
    providing a cylindrical guide having a hollow cylindrical shape and one or more slots extending in a direction of a longitudinal axis of the cylindrical guide;
    placing the cylindrical guide inside the cavity within the medullary canal;
    cutting the one or more slots into the wall of the bone by progressing a saw along edges of the one or more slots of the cylindrical guide.

9. The method of claim 7, wherein the step of cutting one or more slots into the wall of the bone comprises cutting at least two slots into the bone wall extending longitudinally in the direction of the bone and radially outwardly from the medullary canal into the bone wall.

10. The method of claim 7, wherein the slots extend radially outwardly from the medullary canal for the entire thickness of the bone wall.

11. The method of claim 7, wherein in the step of providing the implantable shaft, the plurality of side elements comprises:
    a first set of side elements arranged in spaced longitudinal alignment along and protruding from an outer wall of the central body, the side elements of the first set separated by a first open space disposed between adjacent side elements of the first set, the first open space arranged longitudinally along and radially outside of the outer wall of the central body and in longitudinal and straight linear alignment with the side elements of the first set, wherein ossification occurs through the first open space; and a second set of side elements arranged in spaced longitudinal alignment along and protruding from the outer wall of the central body diametrically opposite the first set, the side elements of the second set separated by a second open space disposed between adjacent side elements of the second set, the second open space arranged longitudinally along and radially outside of the outer wall of the central body and in longitudinal and straight linear alignment with the side elements of the second set, wherein ossification occurs through the second open space.

12. The method of claim 7, wherein the side elements have a thickness that approximates a width of the slots.

13. The method of claim 7, wherein the side elements have a thickness that slightly exceeds a width of the slots.

14. The method of claim 7, wherein the side elements have a width in a radial direction that approximates a thickness of the bone's wall.

15. The method of claim 7, wherein in the step of providing the implantable shaft, the side elements are formed of a solid material, a porous material, a composite material, or a meshed material.

16. The method of claim 7, in the step of providing the implantable shaft, a hole extends through at least one side element of the implantable shaft.

* * * * *